United States Patent [19]

Egerer et al.

[11] Patent Number: 4,681,843
[45] Date of Patent: Jul. 21, 1987

[54] IMMOBILIZATION OF CELLS AND ENZYMES

[75] Inventors: Peter Egerer, Wuppertal; Wulf Crueger, Erkrath; Christian Gölker, Wuppertal, all of Fed. Rep. of Germany

[73] Assignee: Bayer Aktiengesellschaft, Leverkusen, Fed. Rep. of Germany

[21] Appl. No.: 704,350

[22] Filed: Feb. 22, 1985

[30] Foreign Application Priority Data

Mar. 7, 1984 [DE] Fed. Rep. of Germany ....... 3408299

[51] Int. Cl.$^4$ .................. C12P 1/00; C12N 11/04; C12N 11/02; C12N 11/08
[52] U.S. Cl. ..................... 435/41; 435/177; 435/180
[58] Field of Search .......... 435/41, 106, 174, 177, 435/180, 182

[56] References Cited

U.S. PATENT DOCUMENTS

| 4,138,292 | 2/1979 | Chibata et al. | 435/182 X |
| 4,288,552 | 9/1981 | Gestrelius | 435/177 X |
| 4,337,313 | 6/1982 | Hershberger et al. | 435/180 X |
| 4,411,991 | 10/1983 | Hirakawa et al. | 435/106 X |

FOREIGN PATENT DOCUMENTS 0049475 4/1982 European Pat. Off. .
0053764 6/1982 European Pat. Off. .

OTHER PUBLICATIONS

Chemical Abstracts, vol. 95, 1981, p. 273.
Biological Abstracts, vol. 62, No. 3, p. 151.
Biological Abstracts, vol. 62, No. 2, p. 5922.

Primary Examiner—David M. Naff
Attorney, Agent, or Firm—Sprung Horn Kramer & Woods

[57] ABSTRACT

When immobilizing cells and/or enzymes by contact with tannin, epihalohydrin/polyamine copolymer and glutaraldehyde, immobilizing is carried out in the presence of a primary amine. The primary amine is preferably sulfuric acid mono-(2-aminoethyl)-ester, 2-aminoethanol, glycine or tris-(hydroxymethyl)-amino methane. The resulting immobilized cells and/or enzymes retain a higher proportion of their original activity.

14 Claims, 4 Drawing Figures

IMMOBILIZATION OF CELLS AND ENZYMES

A process has been found for the immobilization of cells and enzymes by flocculation and solidification with a polyfunctional aldehyde, which is characterized in that the immobilization is carried out in the presence of low-molecular weight water-soluble monoamines and, if appropriate, in the presence of ammonia.

A process for the immobilization of enzymes in which flocculation is carried out in the presence of bifunctional aldehydes, in particular glutaraldehyde, is already known from U.S. Pat. No. 4,337,313. However, in this process the glutaraldehyde causes a considerable reduction in the enzyme activity. The process according to the invention avoids this disadvantage.

The process according to the invention is based on the use of low-molecular weight water-soluble monoamine compounds in the immobilization, in order to reduce the inactivating influence of aldehydes. The monoamine compound here probably acts as a chemical buffer by binding the aldehyde reversibly as a Schiff's base. The monoamine compounds are not included in the immobilized biomaterial during the flocculation, but are removed together with the excess aldehyde in the washing operation.

Suitable monoamine compounds are water-soluble amines and derivatives thereof, in particular sulphuric acid mono-(2-aminoethyl)ester (I), 2-aminoethanol (II), glycine (III) or tris(hydroxymethyl)aminomethane (IV) of the following formulae:

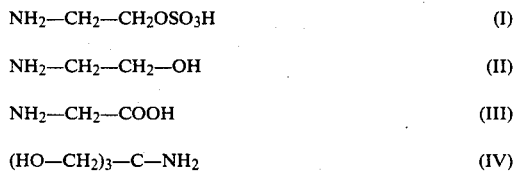

| | |
|---|---|
| $NH_2-CH_2-CH_2OSO_3H$ | (I) |
| $NH_2-CH_2-CH_2-OH$ | (II) |
| $NH_2-CH_2-COOH$ | (III) |
| $(HO-CH_2)_3-C-NH_2$ | (IV) |

Of the possible aldehydes for carrying out the process according to the invention, glutaraldehyde is particularly suitable.

According to the invention, on the addition of the glutaraldehyde-containing solution, the monoamine derivatives mentioned are added, in solid or dissolved form. This can be effected before, after or together with the addition of the glutaraldehyde. The flocculated cells are separated from the mother liquor by sedimentation or centrifugation and washed several times with water. During these washing steps, both excess glutaraldehyde and the protecting amino compound are removed almost entirely. Protection of the enzyme activity from glutaraldehyde by the amino compound is particularly of decisive importance for this working up period, as can be clearly demonstrated with the aid of the comparative examples herein below, the table hereinbelow which lists a number of amino compounds by way of example, and compares their effectiveness in protecting the sucrose mutase from Protaminobacter rubrum from glutaraldehyde, and the accompanying drawings, wherein:

Figure 1:
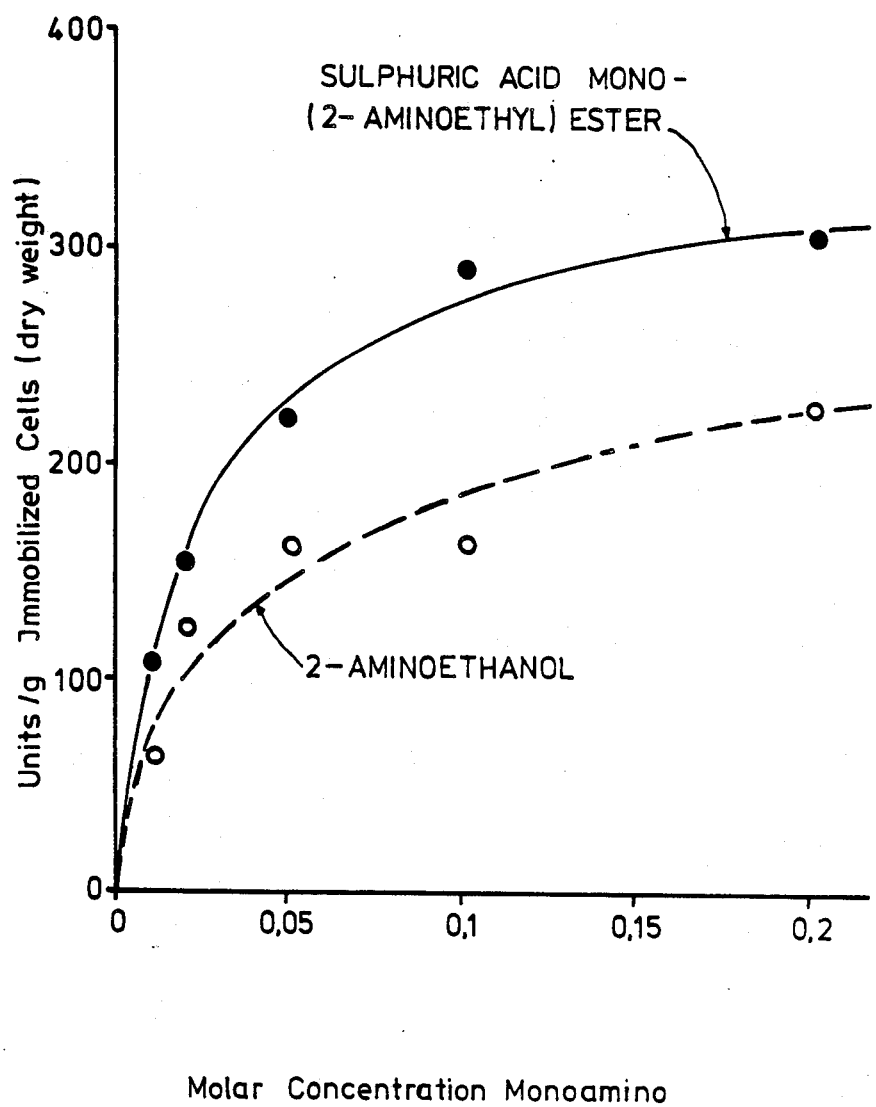
FIG. 1 is a pair of curves showing the effect of different amines on activity at various concentrations.
Figure 2:
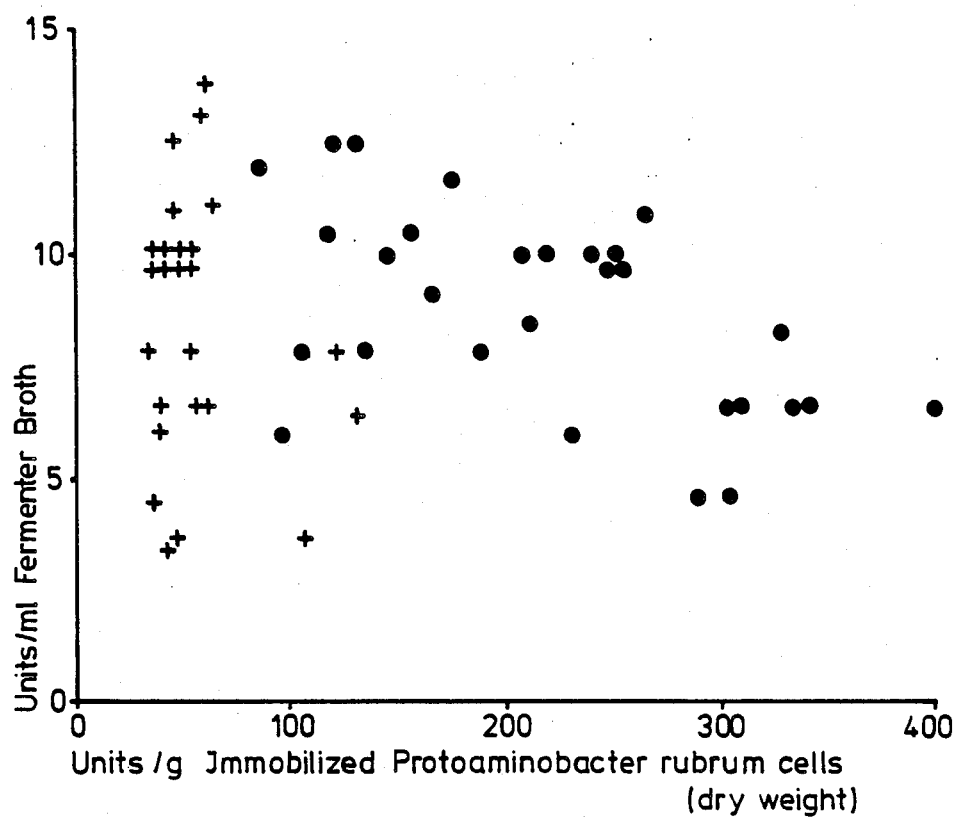
FIG. 2 is a plot of specific activity of one type of cell with and without an additive in accordance with the invention.
Figure 3:
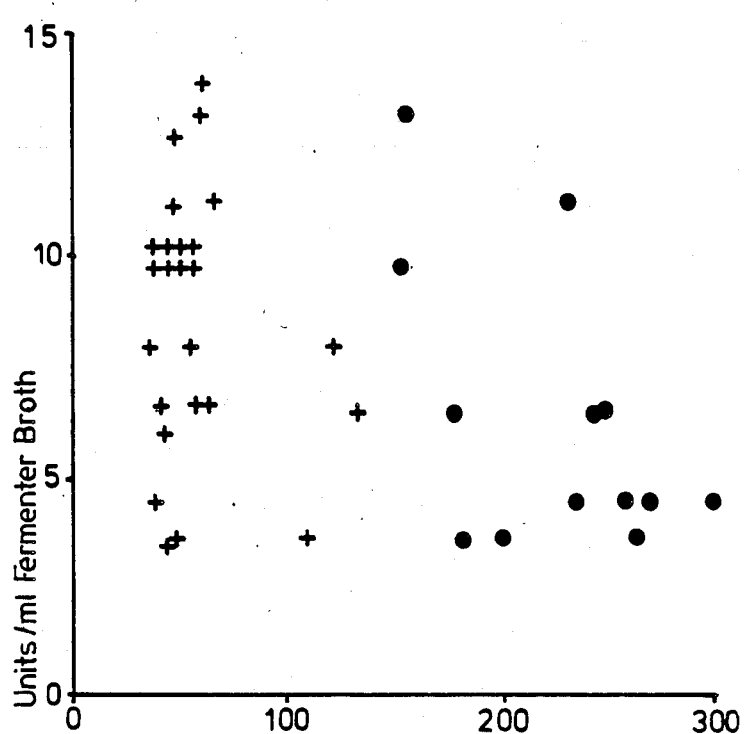
FIG. 3 is a plot similar to FIG. 2 for a different additive.
Figure 4:
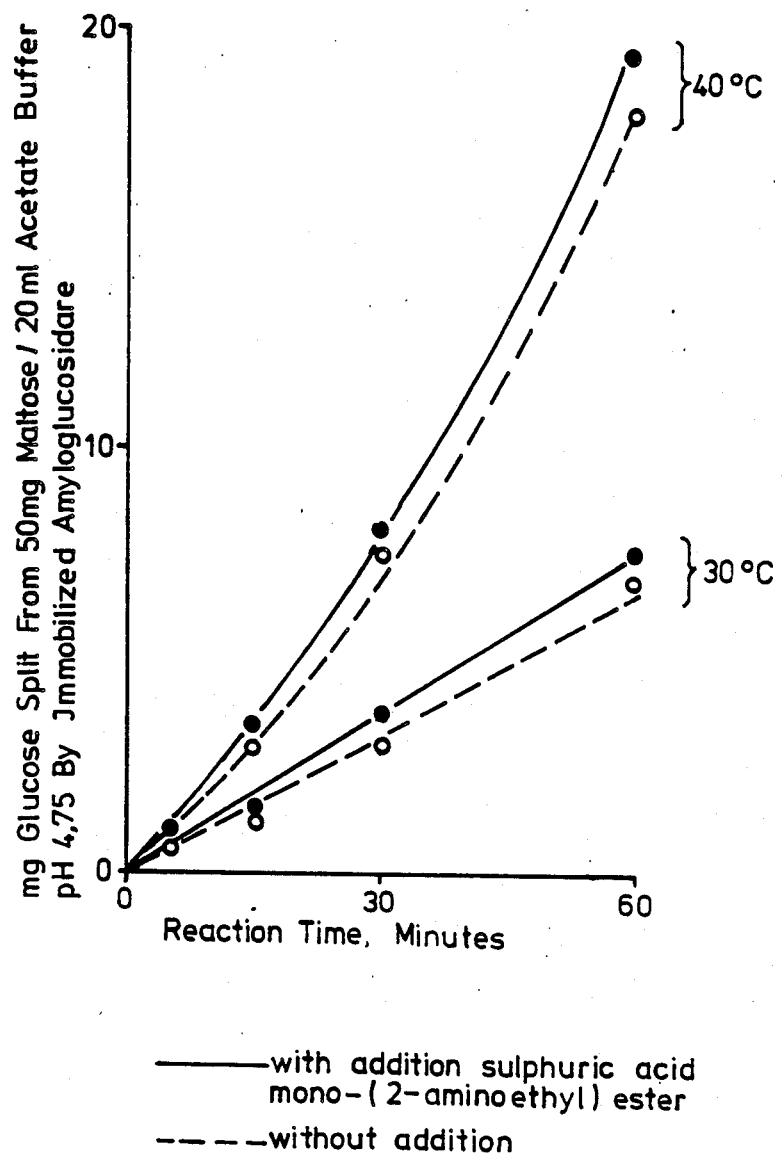
FIG. 4 is a pair of curves showing the effect of one additive at different temperatures.

Referring now more particularly to the drawings, FIG. 1 shows the dependence of the protecting action of amino compounds on concentration, using compounds (I) and (II) as examples. The maximum specific activity is observed between 0.1M and 0.2M amino compound. The specific activities of a large number of immobilization experiments with the amino compounds (I) and (IV) are compared with the specific activities without the addition in FIG. 2 and FIG. 3. The specific activities are in each case plotted against the volume activity of the fermentation broth. The mean values of all the experiments from FIGS. 2 and 3 are 57 units/g for the experiments without the addition, but 224 units/g for experiments with amino compound (IV) and 218 units/g for experiments with amino compound (I). These statistics document the protective influence of the amino compound against glutaraldehyde independently of the individual flocculation method in a large number of experiments.

The mechanical stabilities of the immobilized products with and without the addition of one of the above amino compounds are comparable with one another.

The protecting amino compound according to the invention can also be simultaneously formed directly during fermentation of the cells, that is to say can be prepared in situ by fermentation. For example, amino acid producers, such as *Corynebacterium glutamicum, Brevibacterium flavum, Escherichia coli, Bacillus subtilis* or *Arthrobacter paraffineus* can in this manner be immobilized directly from the fermentation solution and, whilst protected by the amino acid formed during the fermentation, can be crosslinked by means of a bifunctional aldehyde.

The cells and enzymes immobilized by the process according to the invention can be used as biocatalysts for biotransformation reactions.

EXAMPLE 1

Immobilization of *Protaminobacter rubrum* in the presence of sulphuric acid mono-(2-aminoethyl)ester (I)

The strain *Protaminobacter rubrum* Z 12 (CBS 574.77) is used for the production of sucrose mutase. The nutrient solution consists of 5% of sugar beet juice 2% of corn steep liquor and 0.05% of $(NH_4)_2HPO_4$, and the pH value is 7.2. 200 ml of nutrient solution are inoculated with 1 ml of *Protaminobacter rubrum* suspension in a 1 liter conical flask. Fermentation proceeds at 31° C. for 15 hours on a rotary shaking machine.

1 unit of sucrose mutase = 1 μmol/minute conversion of sucrose to isomaltulose.

60 ml of tannin (4%) are added to 1 liter of fermentation broth having an activity of 6.0 units/ml and a pH of 5.5 at 8° C., with stirring, followed by 150 ml of a BETZ/glutaraldehyde mixture (60 g/liter of BETZ, 2.2% v/v of glutaraldehyde, pH 9.0) for complete flocculation of the Protaminobacter cells. (BETZ is a trademark of Betz Laboratories, Inc., Trevase, Pa. It designates an epihalohydrin/polyamine copolymer with a molecular weight of less than one million, containing about 0.288 millimole of amino groups per g of solution see U.S. Pat. No. 4,337,313.) A further 75 ml of the same BETZ/glutaraldehyde mixture are immediately added for crosslinking. The pH value thereby rises to 7.2.

Immediately thereafter, 30 g of solid (I), corresponding to a final concentration of about 0.17M, are stirred in and the pH value is adjusted to 7.2 with 1N NaOH. After the flocks have been centrifuged off, the supernatant liquor is decanted and the sediment is washed with 1 liter of H$_2$O and filtered with suction over a Büchner funnel until as dry as possible. The filter cake is extruded by means of a hand-operated press and dried overnight at 40° to 45° C. A further batch, but without (I), was precipitated and worked up in an identical manner. After grinding and sieving, the middle fraction (particle size of 0.5 to 1.0 mm) of the batch with (I) has an activity of 231.0 units/g, with an activity yield of 23.3%, and that of the batch without (I) has an activity of 41.2 units/g, with an activity yield of 2.8%. The yields were almost identical, at 13.1 g and 13.8 g (in each case dry weights).

EXAMPLE 2

Immobilization of *Protaminobacter rubrum* in the presence of various amounts of (I)

Analogously to Example 1, parallel batches of in each case 1 liter of cell broth (4.6 units/ml) were flocculated, crosslinked in the presence of various concentrations of (I) and worked up. The specific activity was 105.6 units/g, with an activity yield of 7.4%, in the presence of 0.01M (I), 288.5 units/g, with an activity yield of 33.9%, in the presence of 0.1M (I), and 301.8 units/g, with an activity yield of 25.7%, in the presence of 0.2M (I) (compare FIG. 1). The yields (dry weight) before grinding and sieving were 10.2 g, 10.3 g and 10.5 g.

EXAMPLE 3

Immobilization of *Protaminobacter rubrum* in the presence of I and ammonia

In each case 1 liter of cell suspension with an activity of 9.2 units/ml is flocculated and crosslinked in parallel batches. 120 ml of a 4% strength tannin solution are first added to 1 liter of cell suspension, followed by 160 ml of BETZ/glutaraldehyde of Example 1, until flocculation is complete. A further 80 ml of the BETZ/glutaraldehyde mixture, 0.2 mol of (I) and 0.2 mol of ammonia solution are then immediately added to the suspension, with stirring, and the pH value is brought to 8.0. Working up is effected as in Example 1.

Specific activity of the sieve middle fraction: 198.4 g units/g; 25.1% activity yield. Compared with batches without the addition of (I) or with the addition of only (I), this batch has a substantially higher mechanical stability.

Analytical values of two comparison batches: 0.1M (I), 281.9 units/g, 21.4% activity yield; without the addition of amino compounds, 61.4 units/g, 6.0% activity yield. The dry weights before grinding and sieving were almost identical: 20.4 g, 20.3 g, 21.8 g.

EXAMPLE 4

Immobilization of *Serratia plymuthica* in the presence of (I)

The strain *Serratia plymuthica* (ATCC 15928) is used for the production of sucrose mutase. The nutrient solution consists of 5% of viscous juice, 2% of corn steep liquor and 0.05% of (NH$_4$)$_2$HPO$_4$, and the pH value is 7.0. 200 ml of nutrient solution are inoculated with 1 ml of a suspension in a 1 liter conical flask. The fermentation proceeds at 31° C. for 15 hours on a rotary shaking machine.

120 ml of tannin (4%) are added to 1 liter of fermentation broth of 7.2 units/ml and pH 6.5 at 8° C., with stirring, followed by 135 ml of a BETZ/glutaraldehyde mixture according to Example 1, until flocculation is complete. A further 60 ml of the BETZ/glutaraldehyde mixture and 0.2 mol of the amino compound (I) are now added, and the pH value is adjusted to 6.5.

After working up according to Example 1, a specific activity of the sieve middle fraction of 171.2 units/g results.

In contrast, a parallel batch without the addition of (I) exhibits only 69.8 units/g in the sieve middle fraction.

EXAMPLE 5

Immobilization of *Protaminobacter rubrum* in the presence of glycine

*Protaminobacter rubrum* Z 12 CBS 574.77 is grown as in Examples 1 to 3. 1 liter of cell suspension with an activity of 8.2 units/ml is completely flocculated with 120 ml of a 4% strength tannin solution and 170 ml of BETZ/glutaraldehyde mixture according to Example 1. A further 85 ml of BETZ/glutaraldehyde mixture and 0.1 mol of glycine in solid form are then added and the pH value is brought to 6.7. Working up was carried out as described under Example 1.

Specific activity: 232.0 units/g, with an activity yield of 10.2% and a dry weight of 11.5 g before grinding and sieving.

A comparison batch crosslinked without the addition of glycine exhibits 29.9 units/g, with an activity yield of 2.0% and a dry weight of 13.4 g before grinding and sieving.

EXAMPLE 6

Immobilization of *Ptotaminobacter rubrum* in the presence of 2-aminoethanol (II) or tris-(hydroxymethyl)aminomethane (IV). In each case 60 ml of a 4% strength tannin solution are added to in each case 1 liter of fermenter solution of a Protaminobacter rubrum Z 12 (CBS 574.77) culture grown according to Example 1, with an activity of 3.4 units/ml, followed by 100 ml of BETZ/glutaraldehyde mixture, with stirring, until flocculation is complete. In addition to a further 50 ml of this BETZ/glutaraldehyde mixture, 0.2 mol of 2-aminoethanol is added to one of the batches and 0.2 mol of (IV) is added to another batch. The pH values of all the batches are then brought to 7.5 and the batches are worked up as in Example 1.

|  | without addition | 0.2 mol of (II) | 0.2 mol of (IV) |
|---|---|---|---|
| Specific activity units/g | 30.5 | 324.7 | 180.4 |
| Activity yield % | 7 | 58.5 | 23.8 |
| Dry matter g | 13.4 | 11.8 | 9.1 |

EXAMPLE 7

Immobilization of *Escherichia coli* in the presence of (I)

*Escherichia coli* ATCC 9637 is used for the production of penicillin acylase. The nutrient solution consists of 2% of corn steep liquor plus 1% of ammonium phenylacetate, and the pH value is 6.5. 200 ml of nutrient solution are inoculated with 1 ml of an *Escherichia* coli suspension in a 1 liter conical flask. The fermentation proceeds at 31° C. for 20 hours on a rotary shaking machine at 290 rpm. 20 ml of 4% strength tannin solution are first added dropwise to 500 ml of cell suspension, and the suspension is then flocculated completely with the aid of 100 ml of BETZ/glutaraldehyde mixture (60 g/liter of BETZ, 2.2% v/v of glutaraldehyde, pH 9.0). When flocculation is complete, a 50% excess of BETZ/glutaraldehyde are immediately added. Half of the batch is immediately replaced with solid (I) to a final concentration of 0.1M, in addition to the excess of BETZ/glutaraldehyde, and the other half is worked up without (I). After the cell mass has been separated off, washed and extruded, it is dried overnight at 40° to 45° C. and then ground and sieved. Without (I), splitting of penicillin G in 6-aminopenicillanic acid and phenylacetic acid gave a specific activity of 2.17 pen G units per gram of dry catalyst, corresponding to 8.36 NIPAB units/g.

NIPAB is the abbreviation given in the literature for 6-nitro-3-phenylacetamido-benzoic acid, and one NIPAB unit is defined as the activity $$A = \frac{E(405\ nm)}{t \cdot 2.99}\ [\mu mol/minute = 1\ unit]$$

(Kutzbach, C., Rauenbusch, E. (1974) Hoppe-Seyler's Z. Physiol. Chem. 354, 45).

With (I), the specific activity was about 50% higher at 3.29 penicillin G units per gram, corresponding to 12.66 NIPAB units/g.

EXAMPLE 8

**Immobilization of extracellular amyloglucosidase from *Aspergillus foetidus* in the presence of (I)**

*Aspergillus foetidus* ATCC 14 916 is used for the production of amyloglucosidase. The nutrient solution consists of 150 g/liter of corn flour, 50 g/liter of corn steep liquor and 0.2 g/liter of a commercial crude α-amylase. The pH is brought to 6.0 for the sterilization. Before the sterilization, the culture solution is heated to 75° C., cooled and then distributed amongst the fermentation flasks. Sterilization follows at 121° C. for 20 minutes. 200 ml of nutrient solution are inoculated with 5 ml of a spore suspension of *Aspergillus foetidus* in a 1 liter conical flask. The fermentation proceeds at 31° C. for 100 hours on a rotary shaking machine at 290 rpm. 48 ml of 4% strength tannin solution are added dropwise to 800 ml of the fermenter solution centrifuged off, and the solution is inoculated completely by further addition of 20 ml of BETZ/glutaraldehyde mixture according to Example 1, the pH being kept at 6.5. One half is worked up after immediate addition of (I) to a final concentration of 0.1M, and the other half is worked up without (I).

The flocculated amyloglucosidase is dried overnight at 40° to 45° C., ground and sieved. The activity of the dry particles is determined, after preswelling, via the splitting of maltose to give glucose. The glucose released is determined with hexokinase/glucose 6-phosphate dehydrogenase in an enzymatic test.

Specific activity with (I): 9.5 units/g (40° C.); 3.5 units/g (30° C.).

Specific activity without (I): 8.7 units/g (40° C.); 2.8 units/g (30° C.).

TABLE

Comparison of various monoamino compounds in respect of their influence during immobilization of *Protaminobacter rubrum*.

| Addition | Specific activity of immobilized cells |
|---|---|
| None | 45.2 |
| NH$_3$, 0.05 M | 24.6 |
| NH$_3$, 0.10 M | 25.3 |
| NH$_3$, 0.20 M | 23.7 |
| Sulphuric acid mono (2-aminoethyl) ester (I) 0.2 M | 231.0 |
| (I) + NH$_3$, in each case 0.2 M | 198.4 |
| Tris(hydroxymethyl)-aminomethane, 0.2 M (IV) | 180.4 |
| 2-Aminoethanol, 0.2 M (II) | 324.7 |
| 2-Methylaminoethanol, 0.2 M | 25.5 |
| Triethanolamine, 0.2 M | 31.5 |
| N—Methyl-diethanolamine, 0.2 M | 30.5 |
| Glycine, 0.1 M (III) | 232.0 |

It will be understood that the specification and examples are illustrative but not limitative of the present invention and that other embodiments within the spirit and scope of the invention will suggest themselves to those skilled in the art.

We claim:

1. In the immobilization of cells and/or enzymes by flocculation and solidification by contacting the cells and/or enzymes with tannin, epihalohydrin/polyamine copolymer and glutaraldehyde, the improvement which comprises effecting the immobilization in the presence of about 0.05 to 1.0 mole per liter of an added primary amine selected from the group consisting of sulphuric acid mono-(2-aminoethyl)-ester, 2-aminoethanol, glycine and tris-(hydroxymethyl)-aminomethane, followed by removal of the primary amine and excess glutaraldehyde by washing.

2. The process according to claim 1, wherein the monoamine is sulphuric acid mono-(2-aminoethyl)ester.

3. The process according to claim 1, wherein the monoamine is 2-aminoethanol.

4. The process according to claim 1, wherein the monoamine is glycine.

5. The process according to claim 1, wherein the monoamine is tris-(hydroxymethyl)-aminomethane.

6. The process according to claim 1, wherein the monoamine is present in about 0.1 to 0.2 mole per liter.

7. The process according to claim 1, wherein ammonia is also present during the immobilization.

8. The process according to claim 1, wherein the immobilization is carried out at a pH of 5 to 9.

9. The process according to claim 1, wherein cells and/or enzymes of *Protaminobacter rubrum* are immobilized.

10. The process according to claim 1, wherein cells and/or enzymes of *Serratia plymuthica* are immobilized.

11. The process according to claim 1, wherein cells and/or enzymes of *Escherichia coli* are immobilized.

12. The procss according to claim 1, wherein cells and/or enzymes of *Aspergillus foetidus* are immobilized.

13. Immobilized cells and/or enzymes produced according to claim 1.

14. In the carrying out of a biological reaction wherein a reactant is contacted with immobilized cells and/or enzymes produced by immobilization of cells and/or enzymes by flocculation and solidification by contacting the cells and/or enzymes with tannin, epihalohydrin/polyamine copolymer and glutaraldehyde, the improvement which comprises effecting the immobilization in the presence of about 0.05 to 1.0 mole per liter of an added primary amine selected from the group consisting of sulphuric acid mono(2-aminoethyl)-ester, 2-aminoethanol, glycine and tris(hydroxymethyl)-amino-methane, followed by removal of the primary amine and excess glutaraldehyde by washing.

* * * * *